United States Patent [19]
Kawai et al.

[11] Patent Number: 5,798,383
[45] Date of Patent: Aug. 25, 1998

[54] ARYLOXYCYCLOALKENYL AND ARYLOXYIMINOCYCLO-ALKENYLHYDROXYUREAS

[75] Inventors: Akiyoshi Kawai, Handa; Makoto Kawai, Chita-Gun; Rodney W. Stevens, Handa, all of Japan

[73] Assignee: Pfizer Inc., New York, N.Y.

[21] Appl. No.: 836,452

[22] PCT Filed: May 26, 1995

[86] PCT No.: PCT/IB95/00399

§ 371 Date: Jul. 28, 1997

§ 102(e) Date: Jul. 28, 1997

[87] PCT Pub. No.: WO96/15106

PCT Pub. Date: May 23, 1996

[30] Foreign Application Priority Data

Nov. 10, 1994 [WO] WIPO .................. PCT/JP94/1897

[51] Int. Cl.$^6$ .................. A01N 47/28; C07C 67/02; C07C 69/66; C07C 69/76
[52] U.S. Cl. .................. 514/482; 562/623; 560/251; 560/187; 560/106
[58] Field of Search .................. 562/623; 560/251, 560/106, 187; 514/482

[56] References Cited

FOREIGN PATENT DOCUMENTS

| WO 92/09566 | 6/1992 | WIPO | .................. C07C 273/18 |
| WO 94/22814 | 10/1994 | WIPO | .................. C07C 275/64 |
| WO 95/05360 | 2/1995 | WIPO | .................. C07C 275/64 |

*Primary Examiner*—Gary Geist
*Assistant Examiner*—Brian J. Davis
*Attorney, Agent, or Firm*—Peter C. Richardson; Paul H. Ginsburg; Jolene W. Appleman

[57] ABSTRACT

The prevent invention provides a compound of formula (I):

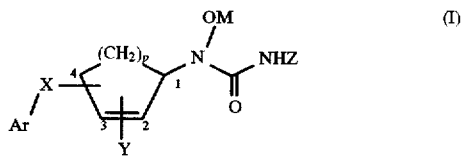

wherein Ar is (a) phenyl, naphthyl and biphenyl, each optionally substituted with $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{2-4}$ alkoxyalkoxy, $C_{1-4}$ alkylthio, hydroxy, halo, cyano, amino, $C_{1-4}$alkylamino, di $(C_{2-8})$ alkylamino, $C_{2-6}$ alkanoylamino, carboxy, $C_{2-6}$ alkoxycarbonyl, or optionally substituted phenyl, phenoxy, phenylthio or phenylsulfinyl or (b) furyl, benzo[b]furyl, thienyl, benzo[b]thienyl, pyridyl or quinolyl, each optionally substituted with $C_{1-4}$ alkyl, $C_{1-4}$ haloalkyl, halo, $C_{1-4}$ alkoxy, optionally-substituted phneyl, phenoxy or phenylthio. X is $C_1$-$C_4$ alkylene, $C_2$-$C_4$ alkenylene, —$(CHR^1)_m$—$Q^1$—$(CHR^2)_n$—, —O—$(CHR^1)_j$—$Q^2$— and —$(CHR^1)$—O—N= in which the N= moiety is attached to the cycloalkene ring; and in which $Q^1$ is O, S, SO, $SO_2$, $NR^3$, CH=N—O or CO, $Q^2$ is O, S, SO, $SO_2$ or $NR^3$, and $R^1$, $R^2$ and $R^3$ are each hydrogen or $C_1$-$C_4$ alkyl, m and n are each an integer from 0 to 4 and j is an integer from 1 to 4; p is an integer of 1 or 2; Y is hydrogen, $C_{1-4}$ alkyl, $C_{1-4}$ haloalkyl, $C_{1-4}$ alkoxy, $C_{2-4}$ alkoxyalkyl, $C_{1-4}$ alkylthio, hydroxy, halo, cyano or amino; Z is hydrogen or $C_{1-4}$ alkyl; and M is hydrogen, a pharmaceutically acceptable cation or a pharmaceutically acceptable metabolically cleavable group.

Further the invention provides a pharmaceutical composition for treating a medical condition for which a 5-lipoxygenase inhibitor is needed in a mammalian subject which comprises a therapeutically effective amount of a compound of the invention and a pharmaceutically acceptable carrier. Preferably the medical condition is an inflammatory disease, allergy or cardiovascular diseases.

8 Claims, No Drawings

ARYLOXYCYCLOALKENYL AND ARYLOXYIMINOCYCLO-ALKENYLHYDROXYUREAS

TECHNICAL FIELD

This invention relates to novel aryloxycycloalkenyl- and aryloxyimino-cycloalkenylhydroxyurea compounds. The compounds of the present invention inhibit the action of 5-lipoxygenase enzyme and are useful in the prevention, treatment or alleviation of inflammatory diseases such as inflammatory bowel disease and rheumatoid arthritis, allergy and cardiovascular diseases in a mammalian subject, e.g., human subject. This invention also relates to pharmaceutical compositions comprising these compounds.

BACKGROUND ART

Arachidonic acid is known to be the biological precursor of several groups of endogenous metabolites, prostaglandins including prostacyclins, thromboxanes and leukotrienes. The first step of the arachidonic acid metabolism is the release of arachidonic acid and related unsaturated fatty acids from membrane phospholipids, via the action of phospholipase $A_2$. Free fatty acids are then metabolized either by cyclooxygenase to produce the prostaglandins and thromboxanes or by lipoxygenase to generate hydroperoxy fatty acids which may be further metabolized to the leukotrienes. Leukotrienes have been implicated in the pathophysiology of inflammatory diseases, including rheumatoid arthritis, gout, asthma, ischemia reperfusion injury, psoriasis and inflammatory bowel diseases. Any drug that inhibits lipoxygenase is expected to provide significant new therapy for both acute and chronic inflammatory conditions.

For a review article on 5-lipoxygenase inhibitors, see H. Masamune and L. S. Melvin, Sr., *Annual Reports in Medicinal Chemistry*, 24 (1989) pp71–80 (Academic Press). More recently, further examples of 5-lipoxygenase inhibitors have been disclosed in International Patent Publication Nos. WO 94/14762 and WO 92/9566.

BRIEF DISCLOSURE OF THE INVENTION

The invention provides a compound of formula (I):

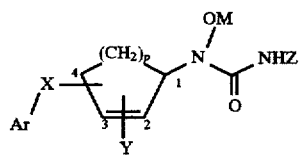

wherein

Ar is selected from the group consisting of:
  (a) phenyl, naphthyl and biphenyl, each optionally substituted with one to three substituents selected from
    $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{2-4}$ alkoxyalkoxy, $C_{1-4}$ alkylthio, hydroxy, halo, cyano, amino, $C_{1-4}$ alkylamino, di ($C_{2-8}$) alkylamino, $C_{2-6}$ alkanoylamino, carboxy, $C_{2-6}$ alkoxycarbonyl, phenyl optionally substituted with one to three substituents selected from $C_{1-4}$ alkyl, $C_{1-4}$ haloalkyl, $C_{1-4}$ alkoxy, $C_{1-4}$ haloalkoxy, cyano and halo, phenoxy optionally substituted with one to three substituents selected from $C_{1-4}$ alkyl, $C_{1-4}$ haloalkyl, $C_{1-4}$ alkoxy, $C_{1-4}$ haloalkoxy, cyano and halo, phenylthio optionally substituted with one to three substituents selected from $C_{1-4}$ alkyl, $C_{1-4}$ haloalkyl, $C_{1-4}$ alkoxy, $C_{1-4}$ haloalkoxy, cyano and halo, and phenylsulfinyl optionally substituted with one to three substituents selected from $C_{1-4}$ alkyl, $C_{1-4}$ haloalkyl, $C_{1-4}$ alkoxy, $C_{1-4}$ haloalkoxy, cyano and halo; and
  (b) furyl, benzo|b|furyl, thienyl, benzo|b|thienyl, pyridyl and quinolyl, optionally substituted with one to three substituents selected from $C_{1-4}$ alkyl, $C_{1-4}$ haloalkyl, halo, $C_{1-4}$ alkoxy, hydroxy, phenyl optionally substituted with one to three substituents selected from $C_{1-4}$ alkyl, $C_{1-4}$ haloalkyl, $C_{1-4}$ alkoxy, $C_{1-4}$ haloalkoxy, cyano and halo, phenoxy optionally substituted with one to three substituents selected from $C_{1-4}$ alkyl, $C_{1-4}$ haloalkyl, $C_{1-4}$ alkoxy, $C_{1-4}$ haloalkoxy, cyano and halo, and phenylthio optionally substituted with one to three substituents selected from $C_{1-4}$ alkyl, $C_{1-4}$ haloalkyl, $C_{1-4}$ alkoxy, $C_{1-4}$ haloalkoxy, cyano and halo;

X is selected from $C_1$–$C_4$ alkylene, $C_2$–$C_4$ alkenylene, —$(CHR^1)_m$—$Q^1(CHR^2)_n$—, —O—$(CHR^1)_j$—$Q^2$— and —$(CHR^1)$—O—N= in which the N= moiety is attached to the cycloalkene ring; and in which $Q^1$ is O, S, SO, $SO_2$, $NR^3$, CH=N—O or CO, $Q^2$ is O, S, SO, $SO_2$ or $NR^3$, and $R^1$, $R^2$ and $R^3$ are each hydrogen or $C_1$–$C_4$ alkyl, m and n are each an integer from 0 to 4 and j is an integer from 1 to 4;

p is an integer of 1 or 2;

Y is hydrogen, $C_{1-4}$ alkyl, $C_{1-4}$ haloalkyl, $C_{1-4}$ alkoxy, $C_{2-4}$ alkoxyalkyl, $C_{1-4}$ alkylthio, hydroxy, halo, cyano or amino;

Z is hydrogen or $C_{1-4}$ alkyl; and

M is hydrogen, a pharmaceutically acceptable cation or a pharmaceutically acceptable metabolically cleavable group.

The compounds of the formula (I) can inhibit the action of 5-lipoxygenase. Therefore the compounds are useful for treating a medical condition for which a 5-lipoxygenase inhibitor is needed, in a mammalian subject, e.g., human subject. The compounds are especially useful for treating inflammatory diseases such as inflammatory bowel disease and rheumatoid arthritis, allergy and cardiovascular diseases.

Accordingly the present invention also provides a pharmaceutical composition for treating a medical condition for which a 5-lipoxygenase inhibitor is needed, e.g., inflammatory diseases such as inflammatory bowel disease and rheumatoid arthritis, allergy and cardiovascular diseases, in a mammalian subject, e.g., human subject, which comprises a therapeutically effective amount of a compound of the invention and a pharmaceutically acceptable carrier.

DETAILED DESCRIPTION OF THE INVENTION

As used herein, the term "pharmaceutically acceptable cation" refers to non-toxic cations, based on alkaline and alkaline earth metals such as sodium, lithium, potassium, calcium and magnesium, as well as those based on non-toxic ammoniums, quaternary ammoniums, including, but not limited to, ammonium, ethylammonium, diethylammonium, triethylammonium, tetraethylammonium, tetramethylammonium and tetrabutylammonium; and the term "metabolically cleavable group" denotes a group which is cleaved in vivo to yield the parent molecule of the structural formula (I) wherein M is hydrogen. Examples of metabolically cleavable groups include —COW, COOW, —CONH$_2$, —CONWW', —CH$_2$OW, —CH(W')OW, —CH$_2$OCOW, —CH$_2$OCO$_2$W, —CH(W')OCO$_2$W radicals where W and W' are each independently selected from (C$_1$-C$_4$) alkyl, phenyl or substituted phenyl wherein the substituent is selected from one or more of C$_1$-C$_4$ alkyl, halogen, hydroxy or C$_1$-C$_4$ alkoxy. Specific examples of representative metabolically cleavable groups include, but are not limited to, acetyl, ethoxycarbonyl, benzoyl and methoxymethyl groups.

Halo includes chloro, bromo, iodo and fluoro, preferably fluoro.

In the above formula (I), Ar is preferably (a), Y and Z are each hydrogen, p is 1 and M is hydrogen or a pharmaceutically acceptable cation.

More preferably, Ar is phenyl, fluorophenyl, cyanophenyl, biphenyl or fluorophenoxyphenyl and X is O which is attached to the 4-position of 2-cyclopentene ring; Ar is phenyl or fluorophenyl and X is —CH=N—O— which is attached to the 4-position of 2-cyclopentene ring; or Ar is phenyl or fluorophenyl and X is —O—N= or —CH$_2$—O—N= which is attached to the 4-position of 2-cyclopentene ring.

A most preferred group of individual compounds includes:

N-{(1R,4R)-trans-4-(4-Fluorophenoxy)-2-cyclopenten-1-yl}-N-hydroxyurea;

N-{(1R,4R)-trans-4-[3-(4-Fluorophenoxy)phenoxy]-2-cyclopenten-1-yl}-N-hydroxyurea;

N-{(1S,4R)-cis-4-[3-(4-Fluorophenoxy)phenoxy]-2-cyclopenten-1-yl}-N-hydroxyurea;

N-{(1R)-4-Benzyloxyimino-2-cyclopenten-1-yl}-N-hydroxyurea; and

N-{(1R)-4-(4-Fluorobenzyloxyimino)-2-cyclopenten-1-yl}-N-hydroxyurea.

The compounds of formula (I) may be prepared by a number of synthetic methods well known in the art. Representative procedures are outlined as follows. In one embodiment, compounds of the formula (I) (M=H) are prepared according to the reaction steps outlined in scheme 1. Ar, X, Y, Z, and p are as previously defined.

SCHEME 1

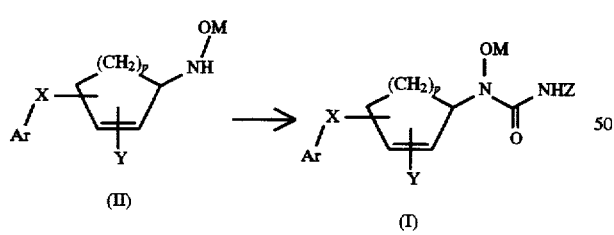

In Scheme 1, the hydroxylamine (II) is treated with a suitable trialkylsilyl isocyanate or lower alkyl isocyanate of the formula ZNCO, in a reaction-inert solvent usually at ambient through to reflux temperature. Preferably the reaction temperature is from 20° to 100° C. Suitable solvents which do not react with reactants and/or products are, for example, tetrahydrofuran, dioxane, methylene chloride or benzene.

An alternative procedure employs treatment of (II) with gaseous hydrogen chloride in a reaction-inert solvent such as benzene or toluene and then subsequent treatment with phosgene. Reaction temperatures are usually in the range of ambient temperature through to boiling point of solvent, preferably 25° to 80° C. The intermediate carbamoyl chloride is not isolated but subjected to (i.e. in situ) reaction with aqueous ammonia or amine ZNH$_2$.

As a modification of this procedure (Z=H) the acid addition salt of (II) may be reacted with an equimolar amount of an alkali metal cyanate, such as potassium cyanate, in water. The product of formula (I) thus obtained is isolated by standard methods and purification can be achieved by conventional means, such as recrystallization and chromatography.

The aforementioned hydroxylamine (II) may be prepared by standard synthetic procedures from a corresponding carbonyl compound, i.e. a ketone or alcohol compound. For example, a suitable carbonyl compound is converted to its oxime and then reduced to the requisite hydroxylamine (II) with a suitable reducing agent (for example, see R. F. Borch et al. *J. Am. Chem. Soc.*, 93, 2897, 1971). Reducing agents of choice are, but not limited to, sodium cyanoborohydride and borane-complexes such as borane-pyridine, borane-triethylamine and borane-dimethylsulfide, however triethylsilane in trifluoroacetic acid may also be employed.

The suitable carbonyl compound, i.e. cyclopentenones, or cyclohexenones, can be prepared by a number of different approaches (see WO 9209566) known to those skilled in the art.

Alternatively, the aforementioned hydroxylamine (II) can easily be prepared by treating the corresponding alcohol with N,O-bis(tert-butyloxycarbonyl)hydroxylamine under Mitsunobu-type reaction conditions followed by acid catalyzed hydrolysis (for example, employing trifluoroacetic acid) of the N,O-protected intermediate product (see JP 1045344). The requisite alcohol is readily prepared by the 1,2-reduction of the corresponding cycloalkenone using a suitable reducing agent such as sodium borohydride, or sodium borohydride-cerium trichloride or the like. Alternatively, the requisite alcohol may be prepared from a suitable cycloalkene diol, for example, commercially available (1S,4R)-cis-4-acetoxy-2-cyclopentene-1-ol and the like, by standard procedures.

The hydroxylamine of formula (II) thus obtained by the abovementioned representative procedures is isolated by standard methods and purification can be achieved by conventional means, such as recrystallization and chromatography.

In another embodiment, compounds of the formula (I) are prepared as illustrated in Scheme 2. R$^4$ is phenyl, and R$^5$ is phenyl or lower alkyl:

SCHEME 2

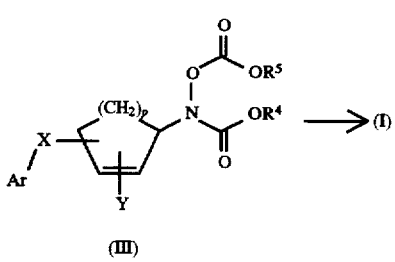

In this process, the compound of formula (III) is prepared from the corresponding alcohol and a bis-carboxyhydroxylamine, preferably N,O-bis (phenoxycarbonyl)hydroxylamine, and subsequently converted to (I) by treatment with ammonia, ammonium hydroxide, or an amine of structure ZNH$_2$ (A. O. Stewart S and D. W. Brooks., *J. Org. Chem.*, 57, 5020, 1992). Suitable reaction solvents for reaction with ammonia, ammonium hydroxide or the amine of formula $ZNH_2$ are, for example, water, methanol, ethanol, tetrahydrofuran, benzene and the like, though reaction may be run in the absence of co-solvent, that is, in requisite amine alone. Reaction temperatures are typically in the range of ambient temperature through to boiling point of solvent. The product of formula (I) thus obtained is isolated by standard methods and purification can be achieved by conventional means, such as recrystallization and chromatography.

The compounds of this invention can exist in stereoisomeric forms by virtue of the presence of one or more chiral centers. The present invention contemplate all such stereoisomers, including enantiomers, diastereomers, and mixtures. The individual isomers of compounds of the formula can be prepared by a number of methods known to those skilled in the art. For instance, they can be prepared by the chiral synthesis from the optically active starting materials. Alternatively, they can be prepared by derivatization of a compound of formula (I) with a chiral auxiliary followed by separation of the resulting diastereomeric mixture and removal of the auxiliary group to provide the desired isomer, or by separation employing a chiral stationary phase.

The pharmaceutically acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent. In the case of non-toxic acid salt, an appropriate mineral or organic acid in either aqueous solution or a suitable organic solvent can be used. The salt may then be obtained by purification or by evaporation of the solvent.

The compounds of formula I inhibit the activity of 5-lipoxygenase enzyme. The ability of the compounds of the formula I to inhibit 5-lipoxygenase enzyme makes them useful for controlling the symptoms induced by the endogenous metabolites arising from arachidonic acid in a mammalian subject, especially human subject. The compounds are therefore valuable in the prevention and treatment of such disease states in which the accumulation of arachidonic acid metabolites are the causative factor; e.g., allergic bronchial asthma, skin disorders, rheumatoid arthritis, osteoarthritis and thrombosis. Thus, the compounds of the formula I and their pharmaceutically acceptable salts are of particular use in the treatment or alleviation of inflammatory diseaes in a human subject.

The ability of the compounds of the formula I to inhibit the activity of the lipoxygenase enzyme may be demonstrated in vitro and in vivo by the following standard procedures.

1) In vitro assay using heparinized human whole blood (HWB)

Inhibition has been demonstrated in vitro using heparinised human whole blood (*British Journal of Pharmacology*: (1990) 99, 113–118), which determines the inhibitory effect of said compounds on 5-lipoxygenase (LO) metabolism of arachidonic acid. Aliquots of heparinized human whole blood (1 ml) from healthy donors were preincubated with drugs dissolved in dimethyl sulfoxide (final concentration, 0.1%) for 10 min at 37° C., then calcium ionophore A21387 (60 µM) and Heparapid (2.5%, Sekisui Chemical Co. LTD., Japan) were added and incubations were continued for further 30 min. Reactions were terminated by rapid cooling in an ice bath. Blood-clots induced by Heparapid were removed by centrifugation. Acetonitrile (ACN, 1.5 ml) and $PGB_2$ (200 ng, as internal standard) were added to supernatants. Samples were mixed by Voltex mixer and precipitated proteins were removed by centrifugation. Supernatants were diluted to 15% ACN with water and were loaded onto prewashed Sep-Pak $C_{18}$ cartridge (Waters Associates, Milford, Miss., U.S.A.) and arachidonate metabolites were eluted with 4 ml of 70% methanol. Methanolic extract was evaporated and the residue was then reconstituted in 250 µl of 67% ACN.

ACN reconstituents (100 µl) were injected onto a reversed phase $C_{18}$ column (Wakosil 5C18, 4.6×50 mm, Wako Pure Chemical Industries LTD, Japan). Column temperature was 40° C. HPLC analysis was performed by Hewlett Packard model 1090M HPLC system. The chromatographic was achieved by gradient elution using two different mobile phase (mobile phase A consisted of 10% ACN, 0.1% trifluoro-acetic acid and 0.05% triethylamine; mobile phase B consisted of 80% ACN, 0.1% trifluoroacetic acid and 0.05% triethylamine). Each mobile phase was continuously sparged with helium. The HPLC gradient was programmed as follows (where A+B=100): from 0 to 9.7 min, a linear gradient from 35 to 100% of mobile phase A with flow rate of 1 ml/min. Peaks of eluting products were quantitated by UV absorbance ($LTB_4$ and $PGB_2$ at 275 nm; HHT and 5-HETE at 235 nm, respectively) and were corrected by $PGB_2$ recovery. Linear regression was used to estimate $IC_{50}$ values.

The compounds of formula I described in the following examples were tested in the aforementioned assay and they were shown to possess the ability to inhibit 5-lipoxygenase activity.

2) In vivo system measuring effects of test compound administered orally against platelet activating factor (PAF) induced lethality in mice The in vivo potency after oral administration of test compounds to ICR mice (male) was determined using the PAF lethality assay in a similar manner as that described in the following articles: J. M. Young, P. J. Maloney, S. N. Jubb, and J. S. Clark, *Prostaglandins*, 30, 545 (1985); M. Criscuoli and A. Subissi, *Br. J. Pharmac.*, 90, 203 (1987); and H. Tsunoda, S. Abe, Y. Sakuma, S. Katayama and K. Katayama, *Prostaglandins Leukotrienes and Essential Fatty Acids*, 39, 291 (1990). PAF was dissolved at a concentration of 1.2 µg/ml in 0.05 mg/ml propranolol-saline containing 0.25% bovine serum albumin (BSA) and injected intravenously into mice at a dose of 12 µg/Kg. Mortality was determined 1 hr after PAF injection. To investigate the effect of 5-LO inhibitors, compounds were dissolved in 5% tween 80, 5% EtOH-saline and administered orally (0.1 ml/10 g) 45 min prior to PAF injection. Linear regression was used to estimate $ED_{50}$ values.

For treatment of the various conditions described above, the compounds of formula I of this invention can be administered to a human subject either alone, or preferably in combination with pharmaceutically acceptable carriers or diluents in a pharmaceutical composition according to standard pharmaceutical practice. The compounds can be administered by various conventional routes of administration including oral, parenteral and by inhalation. When the compound are administered orally, to treat an inflammatory condition in a human subject, the dose range will be from about 0.1 to 10 mg/kg of body weight of the subject to be treated per day, preferably from about 0.5 to 10 mg/kg of body weight per day, in single or divided doses. If parenteral administration is desired, then an effective dose will be from about 0.1 to 1.0 mg/kg of body weight of the human subject to be treated per day. In some instances it may be necessary to use dosages outside these limits, since the dosages will necessarily vary according to the age and response of the individual patient as well as the type and severity of the patient's symptoms and the potency of the particular compound being administered.

For oral administration, the compounds of the invention and their pharmaceutically acceptable salts can be administered, for example, in the form of tablets, powders, lozenges, syrups, capsules, aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifing and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solute should be controlled to make the preparation isotonic. In general, the therapeutically-effective compounds of this invention are present in such dosage forms at concentration levels ranging 5% to 70% by weight, preferably 10% to 50% by weight.

EXAMPLES

The present invention is illustrated by the following examples. However, it should be understood that the invention is not limited to the specific details of these examples.

Melting points were taken with a Büchi melting point apparatus (535) and are uncorrected. Optical rotations were obtained on a JASCO DIP-370 polarimeter. All NMR spectra were measured in $CDCl_3$ by a JEOL NMR spectrometer (JNM-GX270, 270 MHz) unless otherwise indicated and peak positions are expressed in parts per million (ppm) down field from tetramethylsilane. The peak shapes are denoted as follows: s, singlet; d, doublet; t, triplet; q, quartet; quint, quintet; m, multiplet; br, broad.

The following abbreviations are used: Boc for tert-butoxycarbonyl, DMF for dimethylformamide, DMSO for dimethylsulfoxide, THF for tetrahydrofuran, TEA for trifluoroacetic acid.

Example 1

N-{(1R,4R)-trans-4-(4-Fluorophenoxy)-2-cyclopenten-1-yl}-N-hydroxyurea (1R,4R)-trans-4-(4-Fluorophenoxy)-2-cyclopenten-1-yl acetate (step A)

To a stirred solution of 4-fluorophenol (0.785 g; 7 mM), (1S,4R)-cis-4-acetoxy-2-cyclopentene-1-ol (1 g; 7.03 mM), and triphenylphosphine (2.02 g; 7.7 mM) in dry THF (20 ml) was added diisopropyl azodicarboxylate (DPAD; 1.56 g; 7.7 mM) at room temperature (rt). After stirring overnight, volatiles were removed by evaporation. The resulting residue was purified by flash chromatography eluting with ethyl acetate-n-hexane (1:20) to give 1.55 g (94%) of the subtitled compound.

$^1$H-NMR ($CDCl_3$) δ; 6.97 (t, J=8.8 Hz, 2H), 6.82 (dd, J=4.4 Hz, 8.8 Hz, 2H), 6.24 (d, J=5.4 Hz, 1H), 6.16 (d, J=5.4 Hz, 1H), 5.87–5.82 (m, 1H), 5.44–5.38 (m, 1H), 2.40–2.24 (m, 2H), 2.05 (s, 3H).

(1R,4R)-trans-4-(4-Fluorophenoxy)-2-cyclopenten-1-ol (step B)

To a stirred solution of (1R,4R)-4-(4-fluorophenoxy)-2-cyclopenten-1-yl acetate (1.55 g; 6.56 mM) in methanol (10 ml) was added KOH (0.65 g; 9.84 mM) in water (8 ml) at rt. After stirring for 15 min., volatiles were removed by evaporation. The residue was taken up with ethyl acetate (70 ml), and the whole was washed with water (50 ml), brine (50 ml), dried over $MgSO_4$, and concentrated in vacuo to give 1.25 g (98%) of the subtitled compound.

$^1$H-NMR ($CDCl_3$) δ; 6.97 (t, J=8.8 Hz, 2H), 6.82 (dd, J=4.4 Hz, 8.8 Hz, 2H), 6.18–6.12 (m, 2H), 5.44–5.42 (m, 1H), 5.14–5.08 (br.s, 1H), 2.33 (ddd, J=2.9 Hz, 6.6 Hz, 14.3 Hz, 1H), 2.16 (ddd, J=3.3 Hz, 6.6 Hz, 14.3 Hz, 1H), 1.68 (br.s, 1H).

(1S,4R)-cis-4-(4-Fluorophenoxy)-2-cyclopenten-1-yl benzoate (step C)

To a stirred solution of (1R,4R)-trans-4-(4-fluorophenoxy)-2-cyclopenten-1-ol (0.62 g; 3.2 mM) in THF (12 ml) was added triphenylphosphine (0.92 g; 3.51 mM), benzoic acid (0.43 g; 3.51 mM), and DPAD (0.71 g; 3.51 mM) at rt. After stirring overnight, volatiles were removed by evaporation. The residue was purified by flash chromatography eluting with ethyl acetate-n-hexane (1:10) to give 0.82 g (869%) of the subtitled compound.

$^1$H-NMR ($CDCl_3$) δ; 8.04 (dd, J=1.5 Hz, 8.5 Hz, 2H), 7.56 (t, J=7.7 Hz, 1H), 7.43 (t, J=7.7 Hz, 2H), 6.98 (t, J=8.1 Hz, 2H), 6.90–6.84 (m, 2H), 6.29–6.23 (m, 2H), 5.88–5.82 (m, 1H), 5.19–5.15 (m, 1H), 3.08 (quintet, J=7.3 Hz, 1H), 2.02 (dt, J=4.4 Hz, 14.7 Hz, 1H).

(1S,4R)-cis-4-(4-Fluorophenoxy)-2-cyclopenten-1-ol (step D)

To a stirred solution of (1S,4R)-cis-4-(4-fluorophenoxy)-2-cyclopenten-1-yl benzoate (0.82 g; 2.75 mM) in methanol (5 ml) was added KOH (0.27 g; 4.13 mM) in water (4 ml). After stirring for 2 hrs, volatiles were removed by evaporation. The residue was taken up with ethyl acetate (50 ml), and it was washed with water (50 ml). The aqueous layer was extracted with ethyl acetate (40 ml), and the combined organic layers washed with water (50 ml), brine (50 ml), dried over $MgSO_4$, and evaporated in vacuo to give 0.6 g of the subtitled compound.

$^1$H-NMR ($CDCl_3$) δ; 6.98 (t, J=8.8 Hz, 2H), 6.88–6.82 (m, 2H), 6.14 (dd, J=6.2 Hz, 12.8 Hz, 2H), 5.07–5.03 (br.s, 1H), 4.78–4.73 (br.s, 1H), 2.85 (dt, J=7.3 Hz, 14.3 Hz, 2H), 1.78 (dt, J=4.0 Hz, 14.3 Hz, 1H), 1.79 (br.s, 1H).

N,O-bis(tert-Butoxycarbonyl)-N-{(1R,4R)-trans-4-(4-Fluorophenoxy)-2-cyclopenten-1-yl}hydroxylamine (step E)

To a stirred solution of (1S,4R)-cis-4-(4-fluorophenoxy)-2-cyclopenten-1-ol (0.6 g; 2.75 mM) in THF (12 ml) was added triphenylphosphine (0.8 g; 3.025 mM), BocNH-OBoc (0.71 g; 3.025 mM), and DPAD (0.61 g; 3.025 mM) at rt. After stirring for 2 hrs, volatiles were removed by evaporation. The residue was purified by flash chromatography eluting with ethyl acetate-n-hexane (1:10) to give 0.689 g (62%) of the subtitled compound.

$^1$H-NMR ($CDCl_3$) δ; 6.96 (t, J=9.2 Hz, 2H), 6.82 (dd, J=4.4 Hz, 9.2 Hz, 2H), 6.17–6.13 (br.s, 1H), 6.06–6.03 (m, 1H), 5.55–5.48 (br.s, 1H), 5.42–5.35 (br.s, 1H), 2.36 (ddd, J=3.6 Hz, 6.6 Hz, 14.2 Hz, 1H), 2.28–2.15 (br.s, 1H), 1.51 (s, 9H), 1.49 (s, 9H).

N-{(1R,4R)-trans-4-(4-Fluorophenoxy)-2-cyclopenten-1-yl}-N-hydroxyurea (step F)

A solution of N,O-bis(ten-butoxycarbonyl)-N-{(1R,4R)-trans-4-(4-fluorophenoxy)-2-cyclopenten-1- yl}hydroxylamine (0.688 g; 1.68 mM) and TFA (1.3 ml; 16.8 mM) in $CH_2Cl_2$ (5 ml) was stirred for 3 hrs. After removal of volatiles, the residue was taken up with ethyl acetate (80 ml), and the whole was washed with saturated $NaHCO_3$ solution (50 ml), water (50 ml), brine (50 ml), dried over $MgSO_4$, and concentrated in vacuo to give 0.35 g of the hydroxylamine.

To a stirred solution of the hydroxylamine obtained above (0.35 g) in THF (7 ml) was added trimethylsilyl isocyanate (0.3 g; 2.18 mM) at rt. After stirring for 1 hr, ethanol (5 ml) was added, and volatiles were removed by evaporation. The residue was recrystallized from ethyl acetate-n-hexane (2:1) to provide 0.21 g (49%) of the titled compound as colorless crystals.

m.p. 157.5°–158.5° C. (dec). $^1$H-NMR (DMSO-$d_6$) δ; 9.03 (s, 1H), 7.10 (t, J=8.4 Hz, 2H), 6.96–6.91 (m, 2H), 6.41 (s, 2H), 6.10 (d, J=5.2 Hz, 1H), 5.96 (d, J=5.2 Hz, 1H), 5.42–5.35 (br.s, 2H), 2.32–2.25 (m, 1H), 1.94–1.86 (m, 1H). Anal. Calcd. for $C_{12}H_{13}N_2O_3F$: C, 57.14; H, 5.19; N, 11.11. Found: C, 56.99; H, 5.22; N, 11.05.

Example 2

N-{(1S,4R)-cis-4-(4-Fluorophenoxy)-2-cyclopenten-1-yl}-N-hydroxyurea

The titled compound was prepared according to the procedure described in Example 1 using (1R,4R)-trans-4-(4-fluorophenoxy)-2-cyclopenten-1-ol instead of (1S,4R)-cis-4-(4-fluorophenoxy)-2-cyclopenten-1-ol in step E. m.p. 142°–143° C. (dec).

$^1$H-NMR (DMSO-$d_6$) δ; 9.03 (s, 1H), 7.11 (t, J=8.4 Hz, 2H), 6.99–6.93 (m, 2H), 6.40 (s, 2H), 6.03–6.01 (m, 1H), 5.92–5.88 (m, 1H), 5.20–5.15 (m, 2H), 2.66 (dt, J=7.7 Hz, 14.6 Hz, 1H), 1.74 (dt, J=6.3 Hz, 14.6 Hz, 1H). Anal. Calcd. for $C_{12}H_{13}N_2O_3F$: C, 57.14; H, 5.19; N, 11.11. Found: C, 56.99; H, 5.22; N, 11.05.

Example 3

N-{(1R,4S)-cis-4-(4-Fluorophenoxy)-2-cyclopenten-1-yl}-N-hydroxyurea (1S,4S)-trans-4-(4-Fluorophenoxy)-2-cyclopenten-1-ol To a stirred solution of (1S,4R)-cis-4-acetoxy-2-cyclopentene-1-ol (1 g; 7.03 mM) in DMF (10 ml) was added imadazole (1.05 g; 15.48 mM) and tert-butyldimethylsilyl chloride (1.17 g; 7.47 mM) at rt. After stirring overnight, the mixture was poured into water (50 ml). The whole was extracted with ethyl acetate-n-hexane (1:1, 70 ml x2), and the combined organic layers washed with water (50 ml), brine (50 ml), dried over $MgSO_4$, and concentrated in vacuo to give 1.84 g (quant.) of (1R,4S)-cis-4-tert-butyldimethylsilyloxy-2-cyclopenten-1-yl acetate.

$^1$H-NMR (CDCl$_3$) δ; 5.97 (d, J=5.5 Hz, 1H), 5.88 (d, J=5.5 Hz, 1H), 5.46 (t, J=4.0 Hz, 1H), 4.72 (t, J=4.0 Hz, 1H), 2.91 (d, J=2.0 Hz, 1H), 2.80 (q, J=7.0 Hz, 1H), 2.05 (s, 3H), 0.90 (s, 9H), 0.09 (s, 6H).

A stirred suspension of (1R,4S)-cis-4-tert-butyldimethylsilyloxy-2-cyclopenten-1-yl acetate (1.84 g; 7.03 mM) and potassium carbonate (1.46 g; 10.55 mM) in methanol (30 ml) was stirred for 2 hrs. Water (50 ml) was added to the mixture, and the whole was extracted with ethyl acetate (100 ml). The organic layer was washed with water (50 ml), brine (50 ml), dried over $MgSO_4$, and concentrated in vacuo to give 1.65 g (quant.) of (1R,4S)-cis-4-tert-butyldimethylsilyloxy-2-cyclopenten-1-ol.

To a stirred solution of (1R,4S)-cis-4-tert-butyldimethylsilyloxy-2-cyclopenten-1-ol (1.65 g; 7 mM), 4-fluorophenol (0.94 g; 8.4 mM), and triphenylphosphine (2.2 g; 8.4 mM) in THF (20 ml) was added DPAD (1.7 g; 8.4 mM) at rt. After stirring overnight, volatiles were removed by evaporation. Chromatographic purification of the residue eluting with n-hexane provided 1.53 g (71%) of (1S,4S)-trans-4-(4-fluorophenoxy)-1-(tert-butyldimethylsilyloxy)-2-cyclopentene.

$^1$H-NMR (CDCl$_3$) δ; 7.00–6.93 (m, 2H), 6.83–6.78 (m, 2H), 6.07 (s, 2H), 5.42–5.35 (m, 1H), 5.15–5.07 (m, 1H), 2.29 (ddd, J=2.4 Hz, 6.9 Hz, 14.3 Hz, 1H), 2.09 (ddd, J=3.6 Hz, 6.9 Hz, 14.3 Hz, 1H), 0.90 (s, 9H), 0.09 (s, 6H).

To a stirred solution of (1S,4S)-trans-4-(4-fluorophenoxy)-1-(tert-butyldimethylsilyloxy)-2-cyclopentene (1.52 g; 4.94 mM) in dry THF (15 ml) was added tetra-n-butylammonium fluoride (1M. solution in THF; 7.4 ml; 7.4 mM) at rt. After stirring for 2 hrs, volatiles were removed by evaporation. The residue was taken up with ethyl acetate (100 ml), it was washed with water (50 ml), brine (50 ml), dried over $MgSO_4$, and concentrated in vacuo to give 1.34 g of the subtitled compound. $^1$H-NMR (CDCl$_3$) δ; 6.97 (t, J=8.8 Hz, 2H), 6.82 (dd, J=4.4 Hz, 9.1 Hz, 2H), 6.16 (br.s, 2H), 5.46–5.40 (m, 1H), 5.15–5.09 (m, 1H), 2.34 (dq, J=3.3 Hz, 14.3 Hz, 1H), 2.17 (dq, J=3.3 Hz, 14.3 Hz, 1H), 1.64 (br.s, 1H).

N-{(1R,4S)-cis-4-(4-Fluorophenoxy)-2-cyclopenten-1-yl}-N-hydroxyurea

The titled compound was prepared according to the procedure described in Example 1 using (1S,4S)-trans-4-(4-fluorophenoxy)-2-cyclopenten-1-ol instead of (1S,4R)-cis-4-(4-fluorophenoxy)-2-cyclopenten-1-ol in step E.

m.p. 137°–139° C. (dec). $^1$H-NMR (DMSO-$d_6$) δ; 9.03 (s, 1H), 7.11 (t, J=8.4 Hz, 2H), 6.99–6.93 (m, 2H), 6.40 (s, 2H), 6.03–6.01 (m, 1H), 5.92–5.88 (m, 1H), 5.20–5.15 (m, 2H), 2.66 (dt, J=7.7 Hz, 14.6 Hz, 1H), 1.74 (dt, J=6.3 Hz, 14.6 Hz, 1H). Anal. Calcd. for $C_{12}H_{13}N_2O_3F$: C, 57.14; H, 5.19; N, 11.11. Found: C, 57.14; H, 5.21; N, 11.09.

Example 4

N-{(1S,4S)-trans-4-(4-Fluorophenoxy)-2-cyclopenten-1-yl}-N-hydroxyurea

The titled compound was prepared according to the procedure described in Example 1 using (1S,4S)-trans-4-(4-fluorophenoxy)-2-cyclopenten-1-ol instead of (1R,4R)-trans-4-(4-fluorophenoxy)-2-cyclopenten-1-ol in step C.

m.p. 151°–153 ° C. (dec). $^1$H-NMR (DMSO-$d_6$) δ; 9.03 (s, 1H), 7.10 (t, J=8.4 Hz, 2H), 6.93 (dd, J=3.6 Hz, 8.4 Hz, 2H), 6.42 (s, 2H), 6.10 (d, J=5.2 Hz, 1H), 5.96 (d, J=5.2 Hz, 1H), 5.42–5.35 (br.s, 2H), 2.32–2.25 (m, 1H), 1.94–1.86 (m, 1H). Anal. Calcd. for $C_{12}H_{13}N_2O_3F$: C, 57.14; H, 5.19; N, 11.11. Found: C, 56.94; H, 5.21; N, 11.13.

Example 5

N-{(1R,4R)-trans-4-(4-Cyanophenoxy)-2-cyclopenten-1-yl}-N-hydroxyurea

The title compound was prepared according to the procedure described in Example 1 using 4-cyanophenol instead of 4-fluorophenol in step A.

m.p. 162°–163° C. (dec). $^1$H-NMR (DMSO-$d_6$) δ; 9.04 (s, 1H), 7.75 (d, J=7.7 Hz, 2H), 7.10 (d, J=7.7 Hz, 2H), 6.41 (s, 2H), 6.12 (d, J=5.5 Hz, 1H), 6.00 (d, J=5.5 Hz, 1H), 6.57–6.53 (m, 1H), 6.41–6.36 (m, 1H), 2.37–2.27 (m, 1H), 1.99–1.87 (m, 1H). Anal. Calcd. for $C_{13}H_{13}N_3O_3$: C, 60.23; H, 5.05; N, 16.21. Found: C, 60.35; H, 5.06; N, 15.91.

Example 6

N-{(1S,4R)-cis-4-(4-Cyanophenoxy)-2-cyclopenten-1-yl}-N-hydroxyurea

The titled compound was prepared according to the procedure described in Example 2 using (1R,4R)-trans-4-(4-cyanophenoxy)-2-cyclopenten-1-ol instead of (1R,4R)-trans-4-(4-fluorophenoxy)-2-cyclopenten-1-ol.

m.p. 180°–181° C. (dec). $^1$H-NMR (DMSO-$d_6$) δ; 9.03 (s, 1H), 7.75 (d, J=8.0 Hz, 2H), 7.13 (d, J=8.0 Hz, 2H), 6.37 (s, 2H), 6.03 (d, J=5.9 Hz, 1H), 5.94 (d, J=5.9 Hz, 1H), 5.37–5.34 (m, 1H), 5.22–5.17 (m, 1H), 2.77–2.66 (m, 1H), 1.79–1.70 (m, 1H). Anal. Calcd. for $C_{13}H_{13}N_3O_3$: C, 60.23; H, 5.05; N, 16.21. Found: C, 60.54; H, 5.03; N, 16.07.

Example 7

N-[(1R,4R)-trans-4-{3-(4-Fluorophenoxy)phenoxy}-2-cyclopenten-1-yl}-N-hydroxyurea The titled compound was prepared according to the procedure described in Example 1 using 3-(4-fluorophenoxy)phenol instead of 4-fluorophenol in step A.

m.p. 127°–128° C. (dec). $[\alpha]_D$=+195.38° (ethanol, c=0.127). $^1$H-NMR (DMSO-$d_6$) δ; 9.08 (s, 1H), 7.35–7.02 (m, 5H), 6.68 (d, J=8.1 Hz, 1H), 6.48 (s,2H), 6.39 (s, 2H), 6.15–5.88 (m, 2H), 5.39(br.s,2H), 2.35–2.16(m,1H), 2.00–1.80 (m, 1H). Anal. Calcd. for $C_{18}H_{17}N_2O_4F$: C, 62.79; H, 4.98; N, 8.14. Found: C, 62.71; H, 4.93; N, 8.22.

Example 8

N-[(1S,4R)-cis-4-{3-(4-Fluorophenoxy)phenoxy}-2-cyclopenten-1-yl}-N-hydroxyurea The titled compound was prepared according to the procedure described in Example 2 using (1R,4R)-trans-4-{3-(4-fluorophenoxy)phenoxy}-2cyclopentene-1-ol instead of (1R,4R)-trans-4-(4-fluorophenoxy)-2-cyclopentene-1-ol.

m.p. 130°–131° C. (dec). $[\alpha]_D$=41.07° (ethanol, c=0.112). $^1$H-NMR (DMSO-$d_6$) δ; 9.05 (s, 1H), 7.40–7.05 (m, 5H), 6.80–6.45 (m,3H), 6.34 (s, 2H), 6.10–5.85 (m, 2H), 5.30–5.05(m,2H), 2.75–2.55 (m,1H) , 1.85–1.65 (m, 1H). Anal. Calcd. for $C_{18}H_{17}N_2O_4F$: C, 62.79; H, 4.98; N, 8.14. Found: C, 62.67; H, 4.97; N, 8.25.

Example 9

N-[(1S,4R)-cis-4-{-tert-Butyl-5-(4-fluorophenoxy)phenoxy}-2-cyclopenten-1-yl]-N-hydroxyurea The title compound was prepared as a side product in Example 8.

mp: 148°–151° C. $[\alpha]_D$=–54.09 (c=0.12, ethanol). $^1$H-NMR (DMSO-$d_6$) δ: 8.99 (s, 1H), 7.23–7.13 (m, 3H), 7.08–7.02 (m, 2H), 6.67 (d, J=2.2 Hz, 1H), 6.38 (d, J=2.5 Hz, 1H), 6.36 (s, 2H), 6.02 (d, J=5.4 Hz, 1H), 5.90 (d, J=5.4 Hz, 1H), 5.23–5.13 (m, 2H), 2.62–2.49 (m, 1H), 1.88–1.77 (m, 1H), 1.30 (s, 9H). IR (KBr) $cm^{-1}$: 3500, 3380, 2950, 1660, 1580, 1490, 1420, 1200, 1085, 1020, 830. Anal. Calcd. for $C_{22}H_{25}N_2O_4F$ 1/5$H_2O$: C, 65.40; H, 6.34; N, 6.93. Found: C, 65.34; H, 6.28; N, 7.22.

Example 10

N-[(1R,4S)-cis-4-{3-(4-fluorophenoxy)phenoxy}-2-cyclopenten-1-yl|-N-hydroxyurea The title compound was prepared according to the procedure described in Example 3 using 3-(4-fluorophenoxy)phenol instead of 4-fluorophenol.

mp: 133°–135° C. $[\alpha]_D$=+35.50 (c=0.20, ethanol). $^1$H-NMR (DMSO-$d_6$) δ: 9.01 (s, 1H), 7.29–7.20 (m, 3H), 7.13–7.05 (m, 2H), 6.72 (dd, J=2.2 and 8.4 Hz, 1H), 6.54–6.48 (m, 2H), 6.38 (s, 2H), 6.00 (d, J=5.8 Hz, 1H), 5.89 (d, J=5.8 Hz, 1H), 5.21–5.12 (m, 2H), 2.63 (ddd, J=7.7, 7.7 and 13.2 Hz, 1H), 1.75 (ddd, J=5.8, 5.8 and 13.2 Hz, 1H). IR (KBr) $cm^{-1}$: 3300, 2900, 1635, 1610, 1500, 1200, 1140, 845, 785, 760. Anal. Calcd. for $C_{18}H_{17}N_2O_4F$: C, 62.79; H, 4.98; N, 8.14. Found: C, 62.78; H, 5.02; N, 8.05.

Example 11

N-[(1S,4S)-trans-4-{3-(4-fluorophenoxy)phenoxy}-2-cyclopenten-1-yl]-N-hydroxyurea The title compound was prepared according to the procedure described in Example 1 using (1S,4S)-trans-4-{3-(4-fluorophenoxy)phenoxy}-2-cyclopenten-1-ol instead of (1R,4R)-trans-4-(4-fluorophenoxy)-2-cyclopenten-1-ol in step C.

mp: 163°–164° C. $[\alpha]_D$=–172.73 (c=0.10, ethanol). $^1$H-NMR (DMSO-$d_6$) δ: 9.08 (s, 1H), 7.35–7.02 (m, 5H), 6.68 (d, J=8.1 Hz, 1H), 6.48 (bs, 2H), 6.39 (s, 2H), 6.15–5.88 (m, 2H), 5.39 (bs, 2H), 2.35–2.16 (m, 1H), 2.00–1.80 (m, 1H). IR (KBr) $cm^{-1}$: 3450, 3320, 3200, 1620, 1583, 1505, 1485, 1260, 1205, 1140, 1005, 830, 760, 690, 600. Anal. Calcd. for $C_{18}H_{17}N_2O_4F$: C, 62.79; H, 4.98; N, 8.14. Found: C, 62.86; H, 4.99; N, 8.16.

Example 12

N-Hydroxy-N-{(1R,4R)-trans-4-(4-phenylphenoxy)-2-cyclopenten-1-yl}urea

The titled compound was prepared according to the procedure described in Example 1 using 4-phenylphenol instead of 4-fluorophenol in step A.

m.p. 178°–180° C. (dec). $[\alpha]_D$=+181.82° (ethanol, c=0.145). $^1$H-NMR (DMSO-$d_6$) δ; 9.14 (s, 1H), 7.64–7.58 (m, 5H), 7.44 (t, J=7.5 Hz, 2H), 7.31 (t, J=7.3 Hz, 1H), 7.02 (d, J=8.8 Hz, 2H), 6.43 (s, 2H), 6.19–6.14 (m, 1H), 6.00–5.97 (m, 1H), 5.50–5.38 (m, 2H), 2.36–1.90 (m, 2H). Anal. Calcd. for $C_{18}H_{19}N_2O_3$: C, 69.44; H, 6.15; N, 9.00. Found: C, 69.31; H, 5.74; N, 8.83.

Example 13

N-{(1R,4R)-trans-4-(4-Fluorobenzaldehydeoxime-O-2-cyclopentenylether)-1-yl}-N-hydroxyurea 4-Fluorobenzaldehyde oxime O-(1(R), 4(R)-trans-4-hydroxy-2-cyclopenten-1-yl)ether To a stirred solution of (1S,4R)-cis-4-acetoxy-2-cyclopentene-1-ol (2.33 g; 16.4 mM), N-hydroxyphthalimide (2.68 g; 16.4 mM) and triphenylphosphine (4.73 g; 18 mM) in dry THF (50 ml) was added DPAD (3.8 ml; 18 mM) at rt. After stirring for 5 hrs, volatiles were removed by evaporation. The resulting residue was purified by flash chromatography eluting with ethyl acetate-n-hexane (1:4) to give 7.91 g (quant.) of N-((1R,4R)-trans-4-acetoxy-2-cyclopenten-1-oxy)phthalimide.

$^1$H-NMR (CDCl$_3$) δ: 7.85 (dd, J=3.3 Hz, 5.5 Hz, 2H), 7.76 (dd, J=3.3 Hz, 5.5 Hz, 2H), 6.24 (m, 2H), 5.84 (m, 1H), 5.54 (m, 1H), 2.70 (dd, J=3.0 Hz, 7.0 Hz, 1H), 2.19 (dd, J=2.9 Hz, 7.0 Hz, 1H), 2.03 (s, 3H).

To a stirred solution of N-((1R,4R)-trans-4-acetoxy-2-cyclopenten-1-oxy)phthalimide (9.95 g; 32.4 mM) in dry CH$_2$Cl$_2$ (95 ml) was added methylhydrazine (1.8 ml; 32.4

13 mM) at −78° C. under N₂. After stirring for 30 min, the mixture was allowed to warm to rt and stirred for additional 1 hr. The precipitates were filtered off, and the filtrate was evaporated in vacuo to give 5.09 g (quant.) of O-((1R,4R)-trans4-acetoxy-2-cyclopenten-1-yl)hydroxylamine.

¹H-NMR (CDCl₃) δ: 6.19–6.15 (m, 1H), 6.12–6.07 (m, 1H), 5.83–5.77 (m, 1H), 5.60–4.70 (br.s, 2H), 5.03–4.96 (m, 1H), 2.04 (s, 3H), 2.30–1.97 (m, 2H).

A mixture of O-((1R,4R)-trans-4-acetoxy-2-cyclopenten-1-yl)hydroxylamine (5.09 g; 32.4 mM) and 4-fluorobenzaldehyde (3.5 ml; 32.4 mM) in ethanol (90 ml) was stirred at rt for 2 days. After removal of volatiles, the resulting residue was purified by flash chromatography eluting with ethyl acetate-n-hexane (1:20) to give 4.35 g (51%) of 4-fluorobenzaldehyde oxime O-(1(R), 4(R)-trans-4-acetoxy-2-cyclopenten-1-yl)ether.

¹H-NMR (CDCl₃) δ; 8.01 (s, 1H), 7.56 (dd, J=5.5 Hz, 8.8 Hz, 2H), 7.05 (t, J=8.8 Hz, 2H), 6.25–6.12 (m, 2H), 5.87–5.48 (m, 1H), 5.50–5.48 (m, 1H), 2.41 (ddd, J=2.9 Hz, 7.3 Hz, 15 Hz, 1H), 2.17 (ddd, J=3.3 Hz, 7.3 Hz, 15 Hz, 1H), 2.05 (s, 3H).

A mixture of 4-fluorobenzaldehyde oxime O-(1(R), 4(R)-trans-4-acetoxy-2-cyclopenten-1-yl)ether (4.35 g; 16.5 mM) and potassium carbonate (3.43 g; 24.8 mM) in methanol (80 ml) was stirred at rt for 1 hr, and then volatiles were removed by evaporation. Water (100 ml) was added, and the whole was extracted with ethyl acetate (60 ml×2), the combined organic layers washed with water (50 ml), brine (50 ml), dried over MgSO₄, and concentrated in vacuo to give 3.59 g of the subtitled compound.

¹H-NMR (CDCl₃) δ: 8.01 (s, 1H), 7.55 (dd, J=5.5 Hz, 8.8 Hz, 2H), 7.06 (t, J=8.6 Hz, 1H), 6.17–6.12 (m, 2H), 5.51–5.48 (m, 1H), 5.10–5.08 (m, 1H), 2.39 (ddd, J=2.6 Hz, 6.6 Hz, 9.2 Hz, 1H), 2.06 (ddd, J=3.7 Hz, 7.0 Hz, 9.0 Hz, 1H).

N-{(1R,4R)-trans-4-(4-Fluorobenzaldehyde oxime-O-2-cyclopentenyl ether)-1-yl}-N-hydroxyurea The titled compound was prepared according to the procedure described in Example 1 using 4-fluorobenzaldehyde oxime O-(1(R), 4(R)-trans-4-hydroxy-2-cyclopenten-1-yl)ether instead of(1R,4R)-trans-4-(4-fluorophenoxy)-2-cyclopenten-1-ol in step C.

m.p. 150°–151° C. (dec). [α]_D=+313.9° (ethanol, c=0.1). ¹H-NMR (DMSO-d₆) δ: 9.00 (s, 1H), 8.22 (s,1H), 7.70–7.65 (m, 2H), 7.30–7.22 (m, 2H), 6.37 (br.s, 2H), 6.05 (d, J=5.5 Hz, 1H), 5.92 (d, J=5.9 Hz, 1H), 5.35 (m, 2H), 2.28–1.90 (m, 2H). Anal. Calcd. for C₁₃H₁₄N₃O₃F: C, 55.91; H, 5.05; N, 15.05. Found: C, 56.16; H, 4.91; N, 15.27.

Example 14

N-{(1S,4R)-cis-4-(4-Fluorobenzaldehydeoxine-O-2-cyclopentenylether)-1-yl}-N-hydroxyurea The titled compound was prepared according to the procedure described in Example 1 using 4-fluorobenzaldehyde oxime O-(1(R), 4(R)-trans-4-hydroxy-2-cyclopenten-1-yl)ether instead of (1S,4R)-cis-4-(4-fluorophenoxy)-2-cyclopenten-1-ol in step E.

m.p. 148°–149° C. (dec). [α]_D=+49.50 (ethanol, c=0.1). ¹H-NMR (DMSO-d₆) δ: 9.02 (d, J=3.3 Hz, 1H), 8.23 (s,1H), 7.65 (dd, J=2.2 Hz, 12.5 Hz, 2H), 7.25 (t, J=9.0 Hz, 2H), 6.35 (br.s, 2H), 6.02 (t, J=1.8 Hz, 1H), 5.87 (dt, J=1.46 Hz, 5.9 Hz, 1H), 5.30–5.10 (m, 2H), 2.53–2.46 (m, 1H), 1.83 (quint, J=6.6 Hz, 1H). Anal. Calcd. for C₁₃H₁₄N₃O₃F: C; 55.91; H, 5.05; N, 15.05. Found: C, 56.21; H, 4.89; N, 15.19.

14

Example 15

N-{(1R)-4-Benzyloxyimino-2-cyclopenten-1-yl}-N-hydroxyurea (4R)-(E)-4-Hydroxy-2-cyclopentenone oxime-O-benzylether (4R)-4-Acetoxy-2-cyclopentenone was prepared by the oxidation of (1S,4R)-cis-4-acetoxy-2-cyclopentene-1-ol with pyridinium dichromate (PDC) (M. P. Schneider et al., *J. Chem. Soc., Chem. Commun.*, 1298 (1986)). To a stirred solution of (4R)-4-acetoxy-2-cyclopentenone (1.56 g; 11.1 mM) in ethanol (22 ml) was added O-benzylhydroxylamine hydrochloride (1.77 g; 11.1 mM) and pyridine (1.1 ml; 11.1 mM) at rt. After stirring for 3 hrs, volatiles were removed by evaporation. The residue was purified by flash chromatography eluting with ethyl acetate-n-hexane (1:10) to give 2.78 g (quant.) of (4R)-4-acetoxy-2-cyclopentenone oxime-O-benzylether.

¹H-NMR (CDCl₃) δ; 7.37–7.27 (m, 5H), 6.51 (dd, J=2.2 Hz, 5.9 Hz, 1H), 6.43 (dd, J=1.1 Hz, 5.9 Hz, 1H), 5.72 (ddd, J=1.1 Hz, 2.2 Hz, 4.8 Hz, 1H), 5.13 (s, 2H), 3.12 (dd, J=7.0 Hz, 9.1 Hz, 1H), 2.58 (dd, J=2.2 Hz, 9.4 Hz, 1H), 2.05 (s, 3H).

A suspension of (4R)-4-acetoxy-2-cyclopentenone oxime-O-benzylether (2.64 g; 10.8 mM) and potassium carbonate (2.23 g; 16.1 mM) in methanol (80 ml) was stirred overnight at rt. Volatiles were removed by evaporation, and the residue extracted with ethyl acetate (40 ml×2), the combined organic layers washed with water (50 ml), brine (50 ml), dried over MgSO₄, and concentrated in vacuo to give 2.33 g (quant.) of the subtitled compound.

¹H-NMR (CDCl₃) δ; 7.40–7.26 (m, 5H), 6.52 (dd, J=2.2 Hz, 5.5 Hz, 1H), 6.34 (d, J=5.5 Hz, 1H), 5.13 (s, 2H), 4.96 (br.s, 1H), 3.09 (dd, J=7.0 Hz, 18.7 Hz, 1H), 2.48 (dd, J=1.8 Hz, 18.7 Hz, 1H).

N-{(1R)-4-Benzyloxyimino-2-cyclopenten-1-yl}-N-hydroxyurea

The titled compound was prepared according to the procedure described in Example 1 using (4R)-4-hydroxy-2-cyclopentenone oxime-O-benzylether instead of (1R,4R)-trans-4-(4-fluorophenoxy)-2-cyclopenten-1-ol in step C.

m.p. 166°–170° C. (dec). [α]_D=+257.9° (ethanol, c=0.15). ¹H-NMR (DMSO-d₆) δ; 9.18 (d, J=1.1 Hz, 1H), 7.48–7.35 (m, 5H), 6.56 (br.s, 2H), 6.51 (dd, J=2.2 Hz, 5.0 Hz, 1H), 6.41 (dd, J=1.8 Hz, 5.9 Hz, 1H), 5.41 (br.d, J=7.0 Hz, 1H), 5.14 (s, 2H), 2.84 (dd, J=7.7 Hz, 18.3 Hz, 1H), 2.67–2.53 (m, 1H). Anal. Calcd. for C₁₃H₁₅N₃O₃: C, 59.76; H, 5.79; N, 16.08. Found: C, 60.01; H, 5.87; N, 16.

Example 16

N-{(1S)-4-Benzyloxyimino-2-cyclopenten-1-yl}-N-hydroxyurea

The titled compound was prepared according to the procedure described in Example 1 using (4R)-4-hydroxy-2-cyclopentenone oxime-O-benzylether instead of (1S,4R)-cis-4-(4-fluorophenoxy)-2-cyclopenten-1-ol in step E.

m.p. 168°–171° C. (dec). [α]_D=−258.2° (ethanol, c=0.136). ¹H-NMR (DMSO-d₆) δ; 9.18 (d, J=1.1 Hz, 1H), 7.48–7.35 (m, 5H), 6.56 (br.s, 2H), 6.51 (dd, J=2.2 Hz, 5.0 Hz, 1H), 6.41 (dd, J=1.8 Hz, 5.9 Hz, 1H), 5.41 (br.d, J=7.0 Hz, 1H), 5.14 (s, 2H), 2.84 (dd, J=7.7 Hz, 18.3 Hz, 1H), 2.67–2.53 (m, 1H). Anal. Calcd. for C₁₃H₁₅N₃O₃: C, 59.76; H, 5.79; N, 16.08. Found: C, 59.83; H, 5.75; N, 16.

Example 17

N-{(1R)-4-(4-Fluorobenzyloxyimino)-2-cyclopenten-1-yl}-N-hydroxyurea

The titled compound was prepared according to the procedure described in Example 15 using O-(4- fluorobenzyl)hydroxylamine hydrochloride instead of O-benzylhydroxylamine hydrochloride.

m.p. 148°–149° C. (dec). $[\alpha]_D$=+243.75° (ethanol, c=0.128). $^1$H-NMR (DMSO-d$_6$) δ; 9.12 (s, 1H), 7.40 (dd, J=5.9 Hz, 8.4 Hz, 2H), 7.17 (t, J=8.8 Hz, 2H), 6.48–6.31 (m, 4H), 5.34–5.30 (m, 1H), 5.03 (s, 2H), 2.75 (dd, J=7.7 Hz, 14.3 Hz, 1H), 2.54–2.45 (m, 1H). Anal. Calcd. for $C_{13}H_{14}N_3O_3F$: C, 55.91; H, N, 15.05. Found: C, 56.07; H, 5.06; N, 15.03.

Example 18

N-Hydroxy-N-{(1R)-4phenyloxyimino)-2-cyclopenten-1-yl}urea

The titled compound was prepared according to the procedure described in Example 15 using O-phenylhydroxylamine hydrochloride instead of O-benzylhydroxylamine hydrochloride.

m.p. 156°–157° C. (dec). $[\alpha]_D$=+258.0° (ethanol, c=0.1). $^1$H-NMR (DMSO-d$_6$) δ; 9.20 (s, 1H), 7.33 (t, J=7.6 Hz, 2H), 7.16–7.12 (m, 2H), 7.01 (t, J=7.4 Hz, 1H), 6.63 (dd, J=2.2 Hz, 5.9 Hz, 1H), 6.54–6.50 (m, 3H), 5.42 (d, J=7.0 Hz, 1H), 3.00 (dd, J=7.3 Hz, 18.3 Hz, 1H), 2.72 (d, J=18.3 Hz, 1H). Anal. Calcd. for $C_{12}H_{13}N_3O_3$: C, 58.29; H, 5.30; N, 16.99. Found: C, 58.11; H, 5.45; N, 16.41.

We claim:

1. A compound of formula (I):

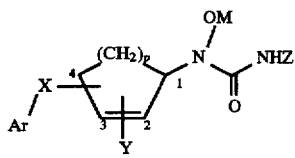

wherein

Ar is selected from the group consisting of:

(a) phenyl, naphthyl and biphenyl, each optionally substituted with one to three substituents selected from
$C_{1-4}$ alkyl, $C_{1-4}$ haloalkyl, $C_{1-4}$ hydroxyalkyl, $C_{1-4}$ alkoxy, $C_{1-4}$ haloalkoxy, $C_{2-4}$ alkoxyalkoxy, $C_{1-4}$ alkylthio, hydroxy, halo, cyano, amino, $C_{1-4}$ alkylamino, di ($C_{2-8}$) alkylamino, $C_{2-6}$ alkanoylamino, carboxy, $C_{2-6}$ alkoxycarbonyl, phenyl optionally substituted with one to three substituents selected from $C_{1-4}$ alkyl, $C_{1-4}$ haloalkyl, $C_{1-4}$ alkoxy, $C_{1-4}$ haloalkoxy, cyano and halo, phenoxy optionally substituted with one to three substituents selected from $C_{1-4}$ alkyl, $C_{1-4}$ haloalkyl, $C_{1-4}$ alkoxy, $C_{1-4}$ haloalkoxy, cyano and halo, phenylthio optionally substituted with one to three substituents selected from $C_{1-4}$ alkyl, $C_{1-4}$ haloalkyl, $C_{1-4}$ alkoxy, $C_{1-4}$ haloalkoxy, cyano and halo, and phenylsulfinyl optionally substituted with one to three substituents selected from $C_{1-4}$ alkyl, $C_{1-4}$ haloalkyl, $C_{1-4}$ alkoxy, $C_{1-4}$ haloalkoxy, cyano and halo; and (b) furyl, benzo[b]furyl, thienyl, benzo[b]thienyl, pyridyl and quinolyl, optionally substituted with one to three substituents selected from $C_{1-4}$ alkyl, $C_{1-4}$ haloalkyl, halo, $C_{1-4}$ alkoxy, hydroxy, phenyl optionally substituted with one to three substituents selected from $C_{1-4}$ alkyl, $C_{1-4}$ haloalkyl, $C_{1-4}$ alkoxy, $C_{1-4}$ haloalkoxy, cyano and halo, phenoxy optionally substituted with one to three substituents selected from $C_{1-4}$ alkyl, $C_{1-4}$ haloalkyl, $C_{1-4}$ alkoxy, $C_{1-4}$ haloalkoxy, cyano and halo, and phenylthio optionally substituted with one to three substituents selected from $C_{1-4}$ alkyl, $C_{1-4}$ haloalkyl, $C_{1-4}$ alkoxy, $C_{1-4}$ haloalkoxy, cyano and halo;

X is selected from $C_1$–$C_4$ alkylene, $C_2$–$C_4$ alkenylene, —(CHR$^1$)$_m$—Q$^1$—(CHR$^2$)$_n$—, —O(CHR$^1$)$_j$—Q$^2$— and —(CHR$^1$)—O—N= in which the N= moiety is attached to the cycloalkene ring; and in which Q$^1$ is O, S, SO, SO$_2$, NR$^3$, CH=N—O or CO, Q$^2$ is O, S, SO, SO$_2$ or NR$^3$, and R$^1$, R$^2$ and R$^3$ are each hydrogen or $C_1$–$C_4$ alkyl, m and n are each an integer from 0 to 4 and j is an integer from 1 to 4;

p is an integer of 1 or 2;

Y is hydrogen, $C_{1-4}$ alkyl, $C_{1-4}$ haloalkyl, $C_{1-4}$ alkoxy, $C_{2-4}$ alkoxyalkyl, $C_{1-4}$ alkylthio, hydroxy, halo, cyano or amino;

Z is hydrogen or $C_{1-4}$ alkyl; and

M is hydrogen, a pharmaceutically acceptable cation or a pharmaceutically acceptable metabolically cleavable group.

2. A compound according to claim 1, wherein Ar is selected from group (a), Y and Z are each hydrogen, p is 1 and M is hydrogen or a pharmaceutically acceptable cation.

3. A compound according to claim 2, wherein Ar is phenyl, fluorophenyl, cyanophenyl, biphenyl or fluorophenoxyphenyl and X is O which is attached to the 4-position of cycloalkene ring.

4. A compound according to claim 2, wherein Ar is phenyl or fluorophenyl, and X is —CH=N—O— which is attached to the 4-position of cycloalkene ring.

5. A compound according to claim 2, wherein Ar is phenyl or fluorophenyl, and X is —O—N= or —CH$_2$—O—N= which is attached to the 4-position of cycloalkene ring.

6. A compound according to claim 1 selected from the group consisting of
N-{(1R,4R)-trans-4-(4-Fluorophenoxy)-2-cyclopenten-1-yl}-N-hydroxyurea;
N-{(1R,4R)-trans-4-[3-(4-Fluorophenoxy)phenoxy]-2-cyclopenten-1-yl}-N-hydroxyurea;
N-{(1S,4R)-cis-4-[3-(4-Fluorophenoxy)phenoxy]-2-cyclopenten-1-yl}-N-hydroxyurea;
N-{(1R)-4-Benzyloxyimino-2-cyclopenten-1-yl}-N-hydroxyurea; and
N-{(1R)-4-(4-Fluorobenzyloxyimino)-2-cyclopenten-1-yl}-N-hydroxyurea.

7. A pharmaceutical composition for treating a medical condition for which a 5-lipoxygenase inhibitor is needed in a mammalian subject which comprises a therapeutically effective amount of a compound of claim 1 and a pharmaceutically acceptable carrier.

8. A method of treating a condition selected from the group consisting of inflammatory disease, allergy and cardiovascular disease in a mammalian subject, comprising administering to said mammalian subject a therapeutically effective amount of a compound of claim 1.

* * * * *